United States Patent [19]

Gaglani et al.

[11] Patent Number: 4,841,064
[45] Date of Patent: Jun. 20, 1989

[54] BACTERICIDAL (3,5-SUBSTITUTED POLYOXYMETHYLENE OXAZOLIDINES

[75] Inventors: Kamlesh Gaglani, Passaic, Albert L. Eilender, Montville, both of N.J.

[73] Assignee: Cosan Chemical Corporation, Carlstadt, N.J.

[21] Appl. No.: 127,552

[22] Filed: Dec. 2, 1987

Related U.S. Application Data

[60] Continuation of Ser. No. 942,041, Dec. 16, 1986, abandoned, which is a continuation of Ser. No. 676,901, Nov. 30, 1984, abandoned, which is a continuation of Ser. No. 418,256, Sep. 15, 1982, abandoned, which is a division of Ser. No. 304,809, Sep. 23, 1981, abandoned.

[51] Int. Cl.$^4$ ............................................. C07D 263/06
[52] U.S. Cl. ...................................... 548/215; 514/374
[58] Field of Search .......................... 548/215; 514/374

[56] References Cited

U.S. PATENT DOCUMENTS

| | | | |
|---|---|---|---|
| 2,571,985 | 10/1951 | Carnes et al. | 548/215 |
| 2,800,487 | 7/1957 | Mark | 548/215 |
| 2,817,663 | 12/1957 | Conlon et al. | 548/215 |
| 3,962,271 | 6/1976 | Sidi et al. | 548/215 |
| 4,012,261 | 3/1977 | Sidi et al. | 548/215 |

OTHER PUBLICATIONS

Mildew Resistance, Fed. Test Method STD No. 141a (1965).
Kotone et al., Chem. Abst. 78-137057d (1973).

*Primary Examiner*—Anton H. Sutto
*Assistant Examiner*—Cecilia Shen
*Attorney, Agent, or Firm*—Pennie & Edmonds

[57] ABSTRACT

This invention discloses a novel class of hydroxyalkyl oxazolidines, and polyoxymethyleneoxazolidines to be used as bactericides in aqueous surface coating compositions.

The compounds have the following structural formulas:

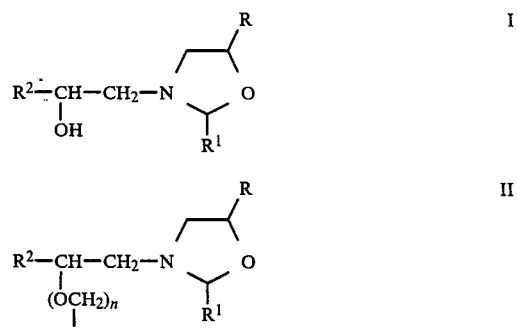

wherein R is hydrogen, an alkyl group of 1 to 6 carbon atoms, a cycloalkyl group of 3 to 8 carbon atoms or an aryl group of 6 to 10 carbon atoms; $R^1$ represents hydrogen, an alkyl group of 1 to 6 carbon atoms, a cycloalkyl group of 3 to 8 carbon atoms, an aryl group of 6 to 10 carbon atoms containing alkyl, halogen, alkoxy, nitro or other substitutuents; $R^2$ represents hydrogen, an alkyl group of 1 to 6 carbon atoms, a cycloalkyl group of 3 to 8 carbon atoms, or an aryl group of 6 to 10 carbon atoms; and n represents an integer in the range of 0 to 8.

7 Claims, No Drawings

BACTERICIDAL (3,5-SUBSTITUTED POLYOXYMETHYLENE OXAZOLIDINES

This is continuation of application Ser. No. 942,041 filed Dec. 16, 1986 which in turn is a continuation of application Ser. No. 676,901 filed Nov. 30, 1984, now abandoned which in turn is a divisional of application Ser. No. 304,809 filed Sept. 23, 1981, now abandoned.

TECHNICAL FIELD

This invention discloses a novel class of hydroxy alkyl oxazolidines, and polyoxymethyleneoxazolidines to be used as bactericides in aqueous surface coating compositions.

The compounds having the following structural formulas:

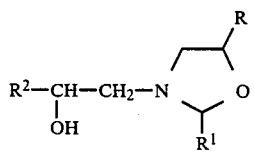

I

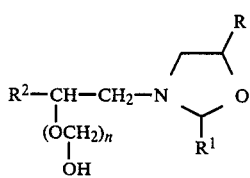

II wherein R is hydrogen, an alkyl group of 1 to 6 carbon atoms, a cycloalkyl group of 3 to 8 carbon atoms or an aryl group of 6 to 10 carbon atoms; $R^1$ represents hydrogen, an alkyl group of 1 to 6 carbon atoms, a cycloalkyl group of 3 to 8 carbon atoms, an aryl group of 6 to 10 carbon atoms, a substituted aryl group of 6 to 10 carbon atoms containing alkyl, halogen, alkoxy, nitro or other substituents; $R^2$ represents hydrogen, an alkyl group of 1 to 6 carbon atoms, a cycloalkyl group of 3 to 8 carbon atoms, or an aryl group of 6 to 10 carbon atoms; and n represents an integer in the range of 0 to 8, preferably 0-4.

BACKGROUND OF THE INVENTION

Aqueous surface coating compositions such as paints, enamels, varnishes and their respective component materials are particularly susceptible to contamination by bacteria and other microorganisms.

Various mono- and bi- cyclic oxymethyleneoxazolidines exhibit biocidal and disinfectant activity and are disclosed in various United States patents, including: 3,890,264; 3,962,271; 4,012,261; 4,022,906; 4,038,284; 4,088,655; 4,138,545; 4,148,905; 4,153,701. These known compounds are substituted at the 2 and in the 4 positions of the ring.

This invention provides a class of hydroxyalkyl oxazolidines and polyoxymethyleneoxazolidines which are characterized by novel structures including substitution at the 3 and in the 5 positions of the ring. The hydroxyalkyl oxazolidines and the resulting polyoxymethyleneoxazolidines are highly effective as antibacterial agents.

SUMMARY OF THE INVENTION

This invention relates to a class of hydroxyalkyl oxazolidines and polyoxymethyleneoxazolidines having structural formulas which include novel substituents at the 3 and 5 positions of the ring:

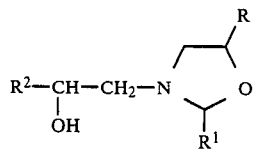

I

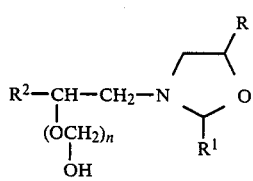

II wherein R is hydrogen, an alkyl group of 1 to 6 carbon atoms, cycloalkyl group of 3 to 8 carbon atoms or an aryl group of 6 to 10 carbon atoms; $R^1$ represents hydrogen, an alkyl group of 1 to 6 carbon atoms, a cycloalkyl group of 3 to 8 carbon atoms, an aryl group of 6 to 10 carbon atoms, a substituted aryl group of 6 to 10 carbon atoms containing alkyl, halogen, alkoxy, nitro or other substituents; $R^2$ represents hydrogen, an alkyl group of 1 to 6 carbon atoms, a cycloalkyl group of 3 to 8 carbon atoms, or an aryl group of 6 to 10 carbon atoms; and n represents an integer in the range of 0 to 8.

The substitutions permit the hydroxyalkyl oxazolidines and polyoxymethyleneoxazolidines to act as highly effective biocidal agents in aqueous surface coating compositions.

DESCRIPTION OF THE INVENTION

The biocidal compounds of this invention are prepared according to the following method:

Preparation of Oxazolidines

The oxazolidines of this invention are prepared by the reaction of an hydroxylated amine having the general formula:

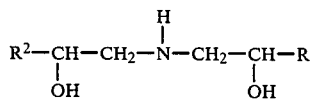

with an aldehyde having the general formula:

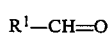

The reaction is carried out in an inert solvent, which forms an azeotrope with water, at reflux. Equimolar portions of amine and aldehyde are preferred. The water of reaction is normally continuously removed. The solvent is removed and the product is distilled at reduced pressure.

The starting hydroxylated amines have the general formula:

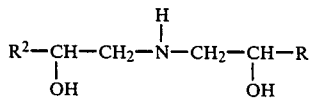

wherein R represents hydrogen, an alkyl group of 1 to 6 carbon atoms, a cycloalkyl group of 3 to 8 carbon atoms or an aryl group of 6 to 10 carbon atoms; and $R^2$ represents hydrogen, an alkyl group of 1 to 6 carbon atoms, a cycloalkyl group of 3 to 8 carbon atoms, or an aryl group of 6 to 10 carbon atoms. Preferably, R and $R^2$ are hydrogen, or lower alkyls of 1 to 6 carbon atoms, particularly methly, ethyl, propyl or butyl. Specific useful hydroxylated amines are: diethanolamine, diisopropanolamine, diisobutanolamine, diisoamylalcoholamine, diisohexanolamine.

The starting aldehydes have the general formula:

$$R^1-CH=0$$

wherein $R^1$ represents hydrogen, an alkyl group of 1 to 6 carbon atoms, a cycloalkyl group of 3 to 8 carbon atoms, an aryl group of 6 to 10 carbon atoms containing alkyl, halogen, alkoxy, nitro or other substituents. Preferably, $R^1$ is a lower alkyl. Specific useful aldehydes are formaldehyde, paraformaldehyde, acetaldehyde, or propionaldehyde.

Preparation of Oxazolidine-Formaldehyde Adducts

The oxazolidines of this invention are prepared according to the above method. Then, one mole of the oxazolidine starting material is reacted with one to eight moles of aqueous formaldehyde and/or paraformaldehyde. The reaction is preferably carried out in an aqueous solution at 25° to 100° C.

The hydroxyalkyl oxazolidines and polyoxymethyleneoxazolidines prepared according to the above methods are advantageously used as biocidal agents in aqueous surface coating compositions. The concentration of the bactericide in the surface coating composition is in the range of 0.005% to 1.0%, preferably 0.05 to 0.35%.

The following Table lists various oxazolidines of this invention. The Table is not limiting in scope, and is intended for the purpose of illustration only.

| Compound | n | R | $R^1$ | $R^2$ |
|---|---|---|---|---|
| 1. (Example 2) | 0 | $CH_3$ | H | $CH_3$ |
| 2. (Example 3) | 1 | $CH_3$ | H | $CH_3$ |
| 3. (Example 4) | 2 | $CH_3$ | H | $CH_3$ |
| 4. (Example 5) | 3 | $CH_3$ | H | $CH_3$ |
| 5. (Example 6) | 4 | $CH_3$ | H | $CH_3$ |
| 6. | 0 | $C_2H_5$ | $CH_3$ | $C_2H_5$ |
| 7. | 0 | $C_3H_7$ | $CH_3$ | $C_3H_7$ |
| 8. | 0 | $C_4H_9$ | $CH_3$ | $C_4H_9$ |

EXAMPLES

The following examples are illustrative and are set forth for the purpose of illustration only and are not to be construed as limiting the scope of the invention in any manner.

EXAMPLE 1

A mixture containing 46.6 g (0.35 m) of diisopropanolamine, 10.8 g (0.35 m) of 97% paraformaldehyde, and 100 cc of toluene was refluxed until 6.3 cc of water was collected in a Barrett tube. The toluene was distilled off and the remaining product was distilled at 78° C. at a pressure of 4.5 mm Hg. The resulting yield of 3-(2-hydroxy)propyl-5-methoxazolidine starting material was 96.6%.

Elemental analysis of the product showed the following:

| | % C | % H | % N | % O |
|---|---|---|---|---|
| Calculated | 57.9 | 10.34 | 9.65 | 22.11 |
| Found | 58.12 | 10.83 | 9.62 | 21.43 |

EXAMPLE 2

A mixture containing 29 g (0.2 m) of 3(2-hydroxy)-propyl-5-methyloxazolidine, 6.6 g (0.2 m) of 91% paraformaldehyde, and 34.4 g of water was refluxed for one hour. The product obtained was an aqueous solution containing 50% water and 50% 3-(2-hydroxymethylene oxy)propyl-5-methyloxazolidine.

Elemental analysis of the product showed the following:

| | % C | % H | % N | % O |
|---|---|---|---|---|
| Calculated | 27.43 | 10.41 | 4.00 | 58.15 |
| Found | 27.21 | 10.45 | 3.96 | 58.38 |

EXAMPLE 3

A mixture containing 29 g (0.2 m) of 3-(2-hydroxy)-propyl-5-methyloxazolidine, 13.2 g (0.4 m) of 91% paraformaldehyde and 39.8 g of water was stirred at reflux for 30 minutes. The product obtained was an aqueous solution containing 50% water and 50% 3-(2-[hydroxymethyloxymethyleneoxy])propyl-5-methyloxazolidine.

Elemental analysis of the product showed the following:

| | % C | % H | % N | % O |
|---|---|---|---|---|
| Calculated | 26.34 | 10.18 | 3.42 | 60.05 |
| Found | 26.16 | 10.21 | 3.39 | 60.24 |

EXAMPLE 4

A mixture containing 29 g (0.2 m) 3-(2 hydroxy-)propyl-5-methyloxazolidine, 18.5 g (0.6 m) of 97% paraformaldehyde and 46.5 g of water was stirred at reflux for one hour. The product obtained was an aqueous solution containing 50% water and 50% 3-[2-(hydroxymethyldioxymethyleneoxy)propyl]-5-methyloxazolidine.

Elemental analysis of the product showed the following:

| | % C | % H | % N | % O |
|---|---|---|---|---|
| Calculated | 25.53 | 10.02 | 2.98 | 61.46 |
| Found | 25.29 | 10.08 | 2.83 | 61.80 |

EXAMPLE 5

A mixture containing 29 g (0.2 m) of 3-(2-hydroxy)-propyl-5-methyloxazolidine, 33 g (1.0 m) of 91% paraformaldehyde and 56 g of water was stirred at reflux for one hour. The product obtained was an aqueous solution containing 50% water and 50% 3-[2-(hydroxymethyltetra(oxymethylene)oxy)propyl]-5-methyloxazolidine.

Elemental analysis of the product showed the following:

|  | % C | % H | % N | % O |
|---|---|---|---|---|
| Calculated | 24.41 | 9.79 | 2.37 | 63.42 |
| Found | 24.49 | 9.72 | 2.34 | 63.45 |

EXAMPLE 6

A mixture containing 29 g (0.2m) of 3-(2-hydroxyl)-propyl-5-methyloxazolidine, 26.4g (0.8 m) of 91% paraformaldehyde and 50.6g of water stirred at reflux for 45 minutes. The product obtained was an aqueous solution containing 50% water and 50% 3-[2-(hydroxymethyl-tri(oxymethylene)oxy)propyl]-5-methyloxazolidine.

Elemental analysis of the product showed the following:

|  | % C | % H | % N | % O |
|---|---|---|---|---|
| Calculated | 24.90 | 9.89 | 2.64 | 62.56 |
| Found | 24.94 | 9.86 | 2.61 | 62.59 |

EXAMPLE 7

The Minimum Inhibitory Concentration Test against *Pseudomonas Aeruginosa* was carried out under the following conditions. The compounds of this invention were added to sterile nutrient broth at 0.1% (1000 ppm) concentration. Each mixture was sequentially diluted with sterile broth to yield various levels of concentrations (500 ppm, 250 ppm, 125 ppm, 62 ppm).

One drop of an actively-growing 24-hour culture of the bacteria was added to each level and the mixture was incubated at 30° C. After 24 hours of incubation, an aliquot from each tube was placed on nutrient agar and observed for growth. The results appear in Table I.

Table I also indicates the results of a test run to show the concentration of test compound required to kill *Pseudomonas Aeruginosa* in 24 hours.

TABLE I
Biological Data on Oxazolidine Derivatives

|  | LEVEL PPM | | | | |
|---|---|---|---|---|---|
|  | 1000 | 500 | 250 | 125 | 62 |
| Minimum Inhibitory Concentration against *Pseudomonas Aeruginosa* | | | | | |
| 1:1 Molar Ratio* | − | − | − | + | + |
| 1:2 Molar Ratio | − | − | − | + | + |
| 1:3 Molar Ratio | − | − | − | + | + |
| 1:4 Molar Ratio | − | − | − | − | + |
| 1:5 Molar Ratio | − | − | − | − | + |
| Oxazolidine** | − | − | − | + | + |
| Concentration Required to Kill *Pseudomonas Aeruginosa* in 24 Hrs. | | | | | |
| 1:1 Molar Ratio* | − | − | + | + | + |
| 1:2 Molar Ratio | − | − | + | + | + |
| 1:3 Molar Ratio | − | − | − | + | + |
| 1:4 Molar Ratio | − | − | − | + | + |
| 1:5 Molar Ratio | − | − | + | + | + |
| Oxazolidine** | − | − | − | + | + |

LEGEND:
− = No Growth
+ = Growth
*In each instance the molar ratio is for the compound to paraformaldehyde
**3-(2-hydroxy)propyl-5-methyloxazolidine

EXAMPLE 8

The anti-bacterial properties of paints containing the compounds of this invention were subsequently evaluated. A latex paint was prepared by following the order of addition listed in the paint formulations in Table II.

TABLE II
PAINT FORMULATION

| RAW MATERIAL | LBS. PEP. 100 GALLONS |
|---|---|
| Water | 200 |
| Ethylene Glycol | 20 |
| Cellulosic Thickener | 3 |
| Dispersant | 6 |
| Surfactant | 2 |
| Defoamer | 1 |
| Bactericide | 2.3 |
| Titanium Dioxide | 250 |
| Magnesium Silicate | 150 |
| Water | 20 |
| Coalescing Agent | 8 |
| Defoamer | 1 |
| Vinyl Acrylic Emulsion | 468 |
|  | 1131.30 |

The bactericide was incorporated before the pigment (titanium dioxide, magnesium silicate) as part of the grind. After 20 minutes, the remaining paint ingredients were added at a slow speed. The paint prepared in this manner contained a 0.2% concentration of oxazolidine or derivatives, as a 50% aqueous solution.

The paints containing the oxazolidines were inoculated with a mixed bacterial culture containing *Escherichia Coli, Pseudomonas Aeruginosa, Proteus Mirabilis,* and *Enterobacter Aerogenes*. Biocidal performance was evaluated at various time intervals by applying a streak of each paint to nutrient agar and recording the results on a growth/no growth basis. The results are listed on Table III.

TABLE III
Anti-Bacterial Evaluation of Oxazolidine Derivatives at 0.2% Versus A Mixed Bacterial Culture of *Pseudomonas Aeruginosa, Escherichia Coli, Proteus Mirabilis, Enterobacter Aerogenes*

|  | 4 HRS | 24 HRS | 48 HRS | 72 HRS | 7 DAYS |
|---|---|---|---|---|---|
|  | FIRST INOCULATION | | | | |
| Blank | 4 | 4 | 4 | 4 | 4 |
| 1:1 Molar Ratio* | 2 | 0 | 0 | 0 | 0 |
| 1:2 Molar Ratio | 0 | 0 | 0 | 0 | 0 |
| 1:3 Molar Ratio | 0 | 0 | 0 | 0 | 0 |
| 1:4 Molar Ratio | 0 | 0 | 0 | 0 | 0 |
| 1:5 Molar Ratio | 0 | 0 | 0 | 0 | 0 |
| Oxazolidine** | 0 | 0 | 0 | 0 | 0 |
|  | SECOND INOCULATION | | | | |
| Blank | 3 | 4 | 4 | 4 | 4 |
| 1:1 Molar Ratio* | 3 | 0 | 0 | 0 | 0 |
| 1:2 Molar Ratio | 2 | 0 | 0 | 0 | 0 |
| 1:3 Molar Ratio | 0 | 0 | 0 | 0 | 0 |
| 1:4 Molar Ratio | 0 | 0 | 0 | 0 | 0 |
| 1:5 Molar Ratio | 0 | 0 | 0 | 0 | 0 |
| Oxazolidine** | 4 | 4 | 4 | 4 | 4 |

LEGEND:
0 = no microbial growth
1 = slight microbial growth
2 = moderate microbial growth
3 = heavy microbial growth
4 = very heavy microbial growth
*In each instance the molar ratio is for the compound to paraformaldehyde
**3-(2-hydroxy)propyl-5-methyloxazolidine

EXAMPLE 9

The physical characteristics of the paint containing the oxazolidines were recorded. A 3 mil wet film drawdown using a Bird Applicator comparing the blank paint (no bactericide) versus the paint containing the biocide was made, and a visual determination of color differences was observed. The results are shown in Table IV.

TABLE IV

PAINT PHYSICAL CHARACTERISTICS OF OXAZOLIDINE DERIVATIVES AT A LEVEL OF 0.2% BIOCIDE ON TOTAL PAINT WEIGHT

| | VISCOSITY(KU) | pH | FILM APPEARANCE |
|---|---|---|---|
| Blank | 78 | 7.5 | OK |
| 1:1 Molar Ratio* | 75 | 7.5 | Slight Yellow |
| 1:2 Molar Ratio | 78 | 7.6 | Slight Yellow |
| 1:3 Molar Ratio | 78 | 7.6 | OK |
| 1:4 Molar Ratio | 78 | 7.6 | OK |
| 1:5 Molar Ratio | 78 | 7.5 | OK |
| Oxazolidine** | 76 | 7.5 | Slight Yellow |

*In each instance the ratio is for the compound to paraformaldehyde
**3-(2-hydroxy)propyl-5-methyloxazolidine

We claim:

1. A class of polyoxymethyleneoxazolidines having the structural formula:

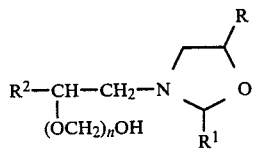

wherein R is an alkyl group of 1 to 6 carbon atoms, a cycloalkyl group of 3 to 8 carbon atoms or an aryl group of 6 to 10 carbon atoms; $R^1$ represents a hydrogen, an alkyl group of 1 to 6 carbon atoms, a cycloalkyl group of 3 to 8 carbon atoms, an aryl group of 6 to 10 carbon atoms, a substituted aryl group of 6 to 10 carbon atoms containing alkyl, halogen, alkoxy, or nitro substituents, $R^2$ represents an alkyl group of 1 to 6 carbon atoms, a cycloalkyl group of 3 to 8 carbon atoms, or an aryl group of 6 to 10 carbon atoms; and n represents an integer in the range of 1 to 8.

2. A polyoxymethyleneoxazolidine according to claim 1 wherein R and $R_2$ represent lower alkyl, and $R^1$ represents hydrogen or lower alkyl.

3. The polyoxymethyleneoxazolidine according to claim 1 comprising 3-(2-hydroxymethyleneoxy)propyl-5-methyloxazolidine.

4. The polyoxymethyleneoxazolidine according to claim 1 comprising 3-[2-(hydroxymethyloxymethyleneoxy)propyl]-5-methyoxazolidine.

5. The polyoxymethyleneoxazolidine according to claim 1 comprising 3-[2-(hydroxymethyl-di(oxymethylene)oxy)propyl]-5-methyloxazolidine.

6. The polyoxymethyleneoxazolidine according to claim 1 comprising 3-[2-(hydroxymethyl-tri(oxymethylene)oxy)propyl]-5-methyloxazolidine.

7. The polyoxymethyleneoxazolidine according to claim 1 comprising 3-[2-(hydroxymethyl-tetra(oxymethylene)oxy)propyl]-5-methyloxazolidine.

* * * * *